(12) United States Patent
Wharton

(10) Patent No.: US 9,044,033 B2
(45) Date of Patent: Jun. 2, 2015

(54) COMPOSITIONS AND METHODS FOR INHIBITING POTATO PATHOGENS

(75) Inventor: Phillip Wharton, Aberdeen, ID (US)

(73) Assignee: UNIVERSITY OF IDAHO, Moscow, ID (US)

( * ) Notice: Subject to any disclaimer, the term of this patent is extended or adjusted under 35 U.S.C. 154(b) by 101 days.

(21) Appl. No.: 13/816,981

(22) PCT Filed: Aug. 15, 2011

(86) PCT No.: PCT/US2011/047811
§ 371 (c)(1),
(2), (4) Date: May 28, 2013

(87) PCT Pub. No.: WO2012/024244
PCT Pub. Date: Feb. 23, 2012

(65) Prior Publication Data
US 2013/0236610 A1 Sep. 12, 2013

Related U.S. Application Data

(60) Provisional application No. 61/373,829, filed on Aug. 14, 2010.

(51) Int. Cl.
*A01N 35/00* (2006.01)
*A23B 7/154* (2006.01)
*A01H 3/00* (2006.01)
*A01N 35/02* (2006.01)
*B65D 81/28* (2006.01)

(52) U.S. Cl.
CPC *A23B 7/154* (2013.01); *A01H 3/00* (2013.01); *A01N 35/02* (2013.01); *B65D 81/28* (2013.01)

(58) Field of Classification Search
CPC ........................................ A01N 35/02
See application file for complete search history.

(56) References Cited

U.S. PATENT DOCUMENTS

| | | | |
|---|---|---|---|
| 4,811,858 A | | 3/1989 | Augur |
| 5,441,735 A | * | 8/1995 | Takahara et al. ............. 424/93.2 |
| 5,547,693 A | | 8/1996 | Krochta et al. |
| 5,698,599 A | | 12/1997 | Subbiah |
| 2007/0149401 A1 | * | 6/2007 | Haskell et al. ................ 504/103 |
| 2007/0207981 A1 | * | 9/2007 | Almenar et al. ................ 514/58 |
| 2009/0060860 A1 | | 3/2009 | Almenar et al. |

FOREIGN PATENT DOCUMENTS

| KR | 20090040193 A | 4/2009 |
|---|---|---|
| WO | 02058464 A2 | 8/2002 |

OTHER PUBLICATIONS

Kajiwara et al., Antimicrobial browning-inhibitory effect of flavor compounds in seaweeds, Journal of Applied Phycology, 2006, pp. 413-422.*
International Preliminary Report received in related foreign application No. PCT/US0211/047811, filed Aug. 15, 2011.
Kajiwara et al., (2006), "Antimicrobial browning-inhibitory effect of flavor compounds in seaweeds," Journal of Applied Phycology, 18:413-422.
Supplementary European Search Report for European Application No. EP 11818629, dated Jul. 4, 2014 (7 pages).

* cited by examiner

*Primary Examiner* — Alton Pryor
(74) *Attorney, Agent, or Firm* — Lathrop & Gage LLP

(57) ABSTRACT

This application relates to compositions and methods for inhibiting the growth of potato pathogens preventing disease during post-harvest storage and processing conditions.

8 Claims, No Drawings

COMPOSITIONS AND METHODS FOR INHIBITING POTATO PATHOGENS

FIELD OF THE DISCLOSURE

Embodiments of the present disclosure are related to compositions and methods for inhibiting the growth of potato pathogens under post-harvest storage conditions.

BACKGROUND OF THE DISCLOSURE

Currently, pesticides are the primary means of controlling postharvest diseases of fruits and vegetables. However, synthetic pesticides have considerable side effects. As well as the phytotoxic and off-odour effects of some prevalent pesticides, high and acute residual toxicity, and long degradation periods, have limited their use. As a result, there has been considerable interest in the use of natural alternatives as food additives to prevent bacterial or fungal growth and to extend the shelf life of foods. Many naturally occurring compounds such as phenols, aldehydes, and organic acids, present in spices and herb extracts, are known to have antimicrobial activity.

Postharvest potato pathogens such as *Erwinia carotovora*, *Colletotrichum coccodes* and *Helminthosporium solani* have become economically important in the table stock market because disease affected potatoes are rejected by processors due to higher tuber health standards demanded by supermarkets and consumers. At present, management of these diseases relies exclusively on frequent applications of foliar fungicides, rather than protecting tubers directly. No effective fungicides (as resistance to thiabendazole is common) are registered for direct application to tubers for control of these important pathogens in storage.

Throughout this description, including the foregoing description of related art, any and all publicly available documents described herein, including any and all U.S. patents, are specifically incorporated by reference herein in their entirety. The foregoing description of related art is not intended in any way as an admission that any of the documents described therein, including pending United States patent applications, are prior art to embodiments of the present disclosure. Moreover, the description herein of any disadvantages associated with the described products, methods, and/or apparatus, is not intended to limit the disclosed embodiments. Indeed, embodiments of the present disclosure may include certain features of the described products, methods, and/or apparatus without suffering from their described disadvantages.

SUMMARY OF THE DISCLOSURE

The present application provides compositions comprising one or more naturally occurring volatiles for use in the prevention, inhibition, or control of postharvest potato pathogens. According to some embodiments, the one or more naturally occurring volatiles may be selected from the group consisting of acetaldehyde, 2-(E)-hexenal, or combinations thereof. In some embodiments, the one or more naturally occurring volatiles may be encapsulated (e.g., micro-encapsulated) in a cyclodextrin (e.g., β-cyclodextrin). See U.S. Publication No. 2009/0060860 and 2007/0207981, incorporated herein by reference in their entireties. The concentration of volatile is between about 0.5 to 50 µL/L (e.g., about 0.5 to 50 µL/L, about 0.5 to 40 µL/L, about 0.5 to 30 µL/L, about 0.5 to 20 µL/L, about 0.5 to 10 µL/L, about 0.5 to 5 µL/L, about 0.5 to 4 µL/L, about 0.5 to 3 µL/L, about 0.5 to 2 µL/L, about 5 to 50 µL/L, about 5 to 40 µL/L, about 5 to 30 µL/L, about 1 to 10 µL/L, about 2 to 10 µL/L, about 3 to 10 µL/L, about 5 to 20 µL/L, or about 5 to 10 µL/L).

According to some embodiments, methods are provided for treating harvested potatoes with one or more naturally occurring volatiles. In some embodiments, methods are provided for treating harvested, unwashed potatoes with one or more naturally occurring volatiles.

According to some embodiments, methods are provided for inhibiting the growth of postharvest potato pathogens on stored harvested potatoes comprising treating harvested potatoes with one or more naturally occurring volatiles. According to some embodiments, methods are provided for inhibiting the growth of postharvest potato pathogens on stored harvested potatoes comprising treating harvested, stored, and/or shipped potatoes with one or more naturally occurring volatiles. In some embodiments, the pathogens may be *Erwinia carotovora*, *Colletotrichum coccodes* and *Helminthosporium solani*.

According to some embodiments, methods are provided for controlling or preventing postharvest disease in stored harvested potatoes comprising treating harvested potatoes with one or more naturally occurring volatiles. According to some embodiments, methods are provided for controlling or preventing postharvest disease in harvested, stored, and/or shipped potatoes comprising treating harvested potatoes with one or more naturally occurring volatiles.

According to some embodiments, methods are provided for extending the storability and shelf-life of potatoes comprising treating harvested, stored, and/or shipped potatoes with one or more naturally occurring volatiles.

According to some embodiments, there is provided a polymeric plastic container or packaging containing one or more naturally occurring volatiles for use in the storage and/or shipping of harvested potatoes. The volatile may be contained in a controlled release mechanism. In some embodiments, the concentration of volatile is between about 0.5 to 50 µL/L (e.g., about 0.5 to 50 µL/L, about 0.5 to 40 µL/L, about 0.5 to 30 µL/L, about 0.5 to 20 µL/L, about 0.5 to 10 µL/L, about 0.5 to 5 µL/L, about 0.5 to 4 µL/L, about 0.5 to 3 µL/L, about 0.5 to 2 µL/L, about 5 to 50 µL/L, about 5 to 40 µL/L, about 5 to 30 µL/L, about 1 to 10 µL/L, about 2 to 10 µL/L, about 3 to 10 µL/L, about 5 to 20 µL/L, or about 5 to 10 µL/L). In some embodiments, the size of the container may be between about 0.1 to 1 L. In some embodiments, the size of the container may be between about 1 to 1,000,000 L (e.g., about 1,000 to 10,000 L; about 10 to 1,000 L; about 50 to 1,000 L; about 100 to 1,000 L; about 10 to 1,000 L; or about 500 to 1,000 L; about 10,000 to 100,000 L; about 100,000 to 1,000,000 L; or about 1 to 10 L).

According to some embodiments, methods are provided for storing harvested potatoes in the presence of one or more naturally occurring volatiles. According to some embodiments, methods are provided for storing harvested potatoes in the presence 2-(E)-hexenal. The concentration of volatile may be between about 0.5 to 50 µL/L (e.g., about 0.5 to 50 µL/L, about 0.5 to 40 µL/L, about 0.5 to 30 µL/L, about 0.5 to 20 µL/L, about 0.5 to 10 µL/L, about 0.5 to 5 µL/L, about 0.5 to 4 µL/L, about 0.5 to 3 µL/L, about 0.5 to 2 µL/L, about 5 to 50 µL/L, about 5 to 40 µL/L, about 5 to 30 µL/L, about 1 to 10 µL/L, about 2 to 10 µL/L, about 3 to 10 µL/L, about 5 to 20 µL/L, or about 5 to 10 µL/L). In some embodiments, the size of the container may be between about 0.1 to 1 L. In some embodiments, potatoes may be stored in a room or container may be between about 1 to 1,000,000 L, or more (e.g., about 1,000 to 10,000 L; about 10 to 1,000 L; about 50 to 1,000 L; about 100 to 1,000 L; about 10 to 1,000 L; or about 500 to 1,000 L; about 10,000 to 100,000 L; about 100,000 to 1,000,000 L; or about 1 to 10 L).

DETAILED DESCRIPTION OF THE INVENTION

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

According to some embodiments, methods are provided for treating harvested potatoes with one or more naturally occurring volatiles. In some embodiments, methods are provided for treating harvested, unwashed potatoes with one or more naturally occurring volatiles.

According to some embodiments, methods are provided for inhibiting the growth of postharvest potato pathogens on stored harvested potatoes comprising treating harvested potatoes with one or more naturally occurring volatiles. According to some embodiments, methods are provided for inhibiting the growth of postharvest potato pathogens on stored harvested potatoes comprising treating harvested, stored, and/or shipped potatoes with one or more naturally occurring volatiles. In some embodiments, the pathogens may be *Erwinia carotovora, Colletotrichum coccodes* and *Helminthosporium solani*.

According to some embodiments, methods are provided for controlling or preventing postharvest disease in stored harvested potatoes comprising treating harvested potatoes with one or more naturally occurring volatiles. According to some embodiments, methods are provided for controlling or preventing postharvest disease in harvested, stored, and/or shipped potatoes comprising treating harvested potatoes with one or more naturally occurring volatiles.

Postharvest pathogens and diseases include the following:

According to some embodiments, methods are provided for extend the storability and shelf-life of potatoes comprising treating harvested, stored, and/or shipped potatoes with one or more naturally occurring volatiles.

According to some embodiments, there is provided methods of treating harvested potatoes with one or more naturally occurring volatiles, wherein the one or more naturally occurring volatile is 2-(E)-hexenal.

According to some embodiments, there is provided methods for inhibiting the growth of postharvest potato pathogens on stored harvested potatoes comprising treating harvested potatoes with one or more naturally occurring volatiles, wherein the one or more naturally occurring volatile is 2-(E)-hexenal. In some embodiments, the pathogen is *Erwinia carotovora, Colletotrichum coccodes* and/or *Helminthosporium solani*.

According to some embodiments, there is provided methods of controlling or preventing postharvest disease in stored harvested potatoes comprising treating harvested potatoes with one or more naturally occurring volatiles, wherein the one or more naturally occurring volatile is 2-(E)-hexenal. In some embodiments, the disease is selected from the group consisting of dry rot, soft rot, leak, late blight, ring rot, pink rot, and silver scurf.

According to some embodiments, there is provided methods of extending the storability and shelf-life of potatoes comprising treating harvested, stored, and/or shipped potatoes with one or more naturally occurring volatiles, wherein the one or more naturally occurring volatile is 2-(E)-hexenal.

According to some embodiments, there is provided methods of storing harvested potatoes comprising storing harvested potatoes in the presence of one or more naturally occurring volatiles, wherein the one or more naturally occurring volatile is 2-(E)-hexenal.

In some embodiments, the concentration of the one or more naturally occurring volatile is between about 0.5 to 50 µL/L.

In some embodiments, the naturally occurring volatile is contained in a controlled release mechanism. In some embodiments, the naturally occurring volatile is encapsu-

| Disease | Causal Agent | Symptoms |
|---|---|---|
| Dry rot | *Fusarium* spp. | brown, firm, sunken flesh; sunken and wrinkled surfaces with blue or white protuberances |
| Soft rot | *Erwinia carotovora* | soft, water cavities in flesh, foul smell; in non-russeted varieties, shallow, round lesions around lenticels |
| Leak | *Pythium* | oozing tubers; well defined areas between healthy and diseased flesh; pink then black flesh with granular, mushy rot |
| Late blight | *Phytophthora infestans* | small, shrunken, dark spots in flesh; foul smell |
| Ring rot | *Cornybacterium sepedonicum* | vascular ring yellow |
| Pink rot | *Phytophthora erythroseptic* | |
| Silver Scurf | *Helminthosporium solani* | The appearance of silver scurf lesions often changes during the storage period. Severe browning of the surface layers of tubers may occur, followed by sloughing-off of the outer layers of the periderm, so that the tuber is protected only by the inner periderm. Lesions have definite margins and are circular, but individual lesions may coalesce as the disease progresses. The silvery appearance of older lesions, for which the disease is named, is most obvious when the tubers are wet and results from air pockets in dead periderm cells. After some time in storage, the surface of the infected tubers may become shriveled and wrinkled due to excessive water loss from the silver scurf lesions. | lated. In some embodiments, the naturally occurring volatile is encapsulated in a cyclodextrin. In some embodiments, the naturally occurring volatile is encapsulated in a β-cyclodextrin.

According to some embodiments, there is provided a polymeric plastic container or packaging containing harvested potatoes and one or more naturally occurring volatiles, wherein the one or more naturally occurring volatile is 2-(E)-hexenal.

In some embodiments, the concentration of the one or more naturally occurring volatile is between about 0.5 to 50 μL/L. In some embodiments, the naturally occurring volatile is contained in a controlled release mechanism. In some embodiments, the naturally occurring volatile is encapsulated. In some embodiments, the naturally occurring volatile is encapsulated in a cyclodextrin. In some embodiments, the naturally occurring volatile is encapsulated in a β-cyclodextrin.

STORAGE

Before storage, potatoes should be culled and cured. Cull and discard any damaged, diseased or frozen tubers. Curing potatoes heals the skin, making it less susceptible to damage and disease. Cure potatoes by exposing them to temperatures between 50 and 60 degrees F. and 95% relative humidity for 10 to 14 days.

Potatoes may be either stored in refrigerated warehouses or non refrigerated bulk bins up to 20 feet deep. In the bulk bins, air should be forced from the floor through corrugated metal ducts up through the pile. This ensures good distribution of cool, humid air, which decreases shrinkage, sprouting, and decay. For table stock, ventilate at 0.6 to 0.7 cubic meters per minute per ton. For chipping stock, use 0.8 to 1 cubic meter per minute per ton. If airflow is too high, the relative humidity surrounding the potatoes may drop, causing weight loss. Air-cooled storage rooms may also be used, but you must ensure that night temperatures are low enough to keep your storage room cool and high enough to prevent freezing.

Hold table potatoes at 38 to 40 degrees F., decreasing field temperature 5 degrees per week to the desired storage temperature. Store processing potatoes at 50 to 55 degrees F., although Russet Burbank for processing can be stored at 45 degrees F. Cool processing potatoes to the final storage temperature at a rate of 3 to 4 degrees per week. Processing potatoes stored below 40 degrees F. will build up sugars that will cause the flesh to turn brown or black when fried. Once the desired holding temperature is reached, keep the temperature differential about 2 degrees F. between the top and bottom of the pile. Do not allow potatoes to remain at temperatures below 30 degrees F., or freezing injury will occur, leading to rot. For all types of potatoes, storage humidity should be 95%, but avoid moisture condensation on tubers and storage walls and ceilings. When diseases such as late blight and Pythium leak are severe, maintain lower humidity during storage and ensure good air circulation.

EXAMPLE 1

In this study, acetaldehyde and 2-(E)-hexenal were chosen as prototype volatiles in order to investigate the use of plant volatiles for the control of potato blemish pathogens in fresh-pack potato packaging. The two main potato blemish disease pathogens, *Colletotrichum coccodes* (black dot) and *Helminthosporium solani* (silver scurf) were used in the study. Cultures of the two pathogens, grown on PDA, were exposed to the pure volatiles in sealed mason jars for 7 days at 23° C. Radial fungal growth and the concentration of the volatile were measured daily and the concentration required to inhibit fungal growth was determined. The objectives of this study were to determine the optimal concentrations of plant volatiles required to inhibit fungal growth, which volatile was more effective, and to determine whether the volatiles are fungistatic and fungitoxic or both. Preliminary results demonstrate that the use of these volatile compounds in active packaging systems for the control of potato blemish diseases. 2-(E)-hexenal showed nearly complete inhibition of three postharvest potato pathogens, *Erwinia carotovora, Colletotrichum coccodes* and *Helminthosporium solani*. 2-(E)-hexenal could be used to control these and other pathogens and extend the storability and shelf-life of potatoes.

EXAMPLE 2

Acetylaldehyde and 2-(E)-hexenal were chosen as prototype volatiles to investigate the use of plant volatiles for the control of potato blemish pathogens. Three main potato blemish pathogens were used in the study: *Erwinia carotovora, Colletotrichum coccodes* and *Helminthosporium solani*.

The objectives of this study were to determine the optimal concentration plant volatiles required to inhibit pathogenic growth, which volatile was more effective and whether the volatiles were toxic and static.

1 L jars were used. Pure volatile (2.5-10 μL/L) was inserted into the jars onto the side of the jar above 6 cm plates containing the pathogens. Controls and treatments were incubated at 23 degree C. until the control filled the plate. Diameter of the colony (mm) from control and treatments were evaluated daily using calipers.

2-E-Hexenal shows nearly complete inhibition for the tested postharvest pathogens at a low concentration of 2.5 μL/L.

What is claimed is:

1. A method for inhibiting or controlling the growth of postharvest potato pathogens on stored harvested potatoes comprising treating harvested potatoes with a naturally occurring volatile effective at inhibiting or controlling the growth of the postharvest potato pathogens on the harvested potatoes, wherein the naturally occurring volatile comprises 2-(E)-hexenal (trans-2-hexenal) and wherein the postharvest potato pathogens comprise *Colletotrichum coccodes*.

2. The method of claim 1, wherein the postharvest potato pathogens further comprise *Erwinia carotovora* and *Helminthosporium solani*.

3. The method of claim 1, further comprising inhibiting or controlling postharvest disease in stored harvested potatoes, wherein the postharvest disease is black dot.

4. The method of claim 1, wherein the concentration of the 2-(E)-hexenal is between about 0.5 to 50 μl/L.

5. The method of claim 1, wherein the 2-(E)-hexenal is contained in a controlled release mechanism.

6. The method of claim 1, wherein the 2-(E)-hexenal is encapsulated.

7. The method of claim 6, wherein the 2-(E)-hexenal is encapsulated in a cyclodextrin.

8. The method of claim 7, wherein the 2-(E)-hexenal is encapsulated in a β-cyclodextrin.

\* \* \* \* \*